US012472325B2

(12) United States Patent
Cordts et al.

(10) Patent No.: US 12,472,325 B2
(45) Date of Patent: Nov. 18, 2025

(54) ADAPTER FOR ESTABLISHING A FLOW CHANNEL BETWEEN A BREATHING GAS SUPPLY AND A PATIENT CONNECTOR

(71) Applicant: Drägerwerk AG & Co. KGaA, Lübeck (DE)

(72) Inventors: Sandra Cordts, Lübeck (DE); Daniel Schmidt, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 863 days.

(21) Appl. No.: 17/741,082

(22) Filed: May 10, 2022

(65) Prior Publication Data

US 2022/0362504 A1 Nov. 17, 2022

(30) Foreign Application Priority Data

May 11, 2021 (DE) ..................... 10 2021 112 254.6

(51) Int. Cl.
*A61M 16/08* (2006.01)
*A61M 16/10* (2006.01)
*A61M 16/20* (2006.01)

(52) U.S. Cl.
CPC ...... *A61M 16/0833* (2014.02); *A61M 16/104* (2013.01); *A61M 16/105* (2013.01);
(Continued)

(58) Field of Classification Search
CPC .. A61M 16/085; A61M 16/20; A61M 16/208; A61M 16/209; A61M 16/0841; A61M 16/0858; A61M 16/0866; A61M 16/104; A61M 16/105; A61M 16/1095; A61M 16/0816; A61M 2016/103; A61M 2240/00; Y10T 137/2642; Y10T 137/7909;
(Continued)

(56) References Cited

U.S. PATENT DOCUMENTS 3,661,528 A * 5/1972 Falk ..................... G01N 33/497
73/863.86
4,406,291 A 9/1983 Schwesinger
(Continued)

FOREIGN PATENT DOCUMENTS

CN 101171049 A 4/2008
CN 103768734 A 5/2014
(Continued)

*Primary Examiner* — Colin W Stuart
*Assistant Examiner* — Douglas Y Sul
(74) *Attorney, Agent, or Firm* — McGlew and Tuttle, P.C.

(57) ABSTRACT

An adapter (1) for establishes a flow channel (2) between a breathing gas supply and a patient connection piece. A set (20) and a system (30) for ventilation or respiratory support, each include the adapter (1). The adapter (1) includes a first connection structure (3) configured to connect to the breathing gas supply and a second connection structure (4) configured to connect to a patient connection piece. A bypass channel (5) branches off from the flow channel (2) and is provided with an extraction opening (7) which can be closed at least temporarily by a safety valve (6). The safety valve (6) is configured such that the extraction opening (7) is closed when a ventilation pressure prevailing in the flow channel (2) is lower than a pressure prevailing on a side of the safety valve facing away from the flow channel (2).

20 Claims, 3 Drawing Sheets

(52) U.S. Cl.
CPC ...... *A61M 16/1095* (2014.02); *A61M 16/209* (2014.02); *A61M 16/085* (2014.02)

(58) Field of Classification Search
CPC ........... Y10T 137/791; Y10T 137/7925; Y10T 137/7929; Y10T 137/87788
USPC ....... 137/112.26, 533, 533.11, 538, 540, 870
See application file for complete search history.

(56) References Cited

U.S. PATENT DOCUMENTS 5,305,762 A * 4/1994 Acorn .................... A61B 5/097 600/529
5,357,951 A * 10/1994 Ratner ................ A61M 16/085 128/205.12
5,642,726 A 7/1997 Owens et al.
8,821,409 B2 * 9/2014 Ku ....................... G01N 33/497 600/529
2009/0281443 A1 11/2009 Hengstenberg et al.
2011/0098592 A1 4/2011 Colman et al.
2017/0325716 A1 * 11/2017 Coleman ................ A61B 5/082
2019/0125993 A1 5/2019 Kemps et al.
2019/0269873 A1 * 9/2019 Rodiera Olivé ...... A61M 16/01
2019/0274588 A1 * 9/2019 Cardin .............. A61M 16/0057

FOREIGN PATENT DOCUMENTS

| | | | |
|---|---|---|---|
| CN | 104258491 | A | 1/2015 |
| CN | 110520183 | A | 11/2019 |
| CN | 110960765 | A | 4/2020 |
| CN | 212997880 | U | 4/2021 |
| DE | 4130724 | A1 | 3/1993 |
| WO | 9101771 | A1 | 2/1991 |
| WO | 2015168377 | A1 | 11/2015 |
| WO | 2018047058 | A1 | 3/2018 |

* cited by examiner

ADAPTER FOR ESTABLISHING A FLOW CHANNEL BETWEEN A BREATHING GAS SUPPLY AND A PATIENT CONNECTOR

CROSS REFERENCE TO RELATED APPLICATIONS

This application claims the benefit of priority under 35 U.S.C. § 119 of German Application 10 2021 112 254.6, filed May 11, 2021, the entire contents of which are incorporated herein by reference.

TECHNICAL FIELD

The invention relates to an adapter for establishing a flow channel between a breathing gas supply and a patient connector, and to both a ventilation or respiratory support set and a ventilation or respiratory support system, each having such an adapter. The described adapter has a first connection structure for connection to the breathing gas supply and a second connection structure for connection to a patient connector piece.

TECHNICAL BACKGROUND

In the field of anesthesia, intensive care and emergency medicine, it is now common practice to measure the end-tidal carbon dioxide content (etCO2) in the respiratory gas (breathing gas), i.e. the carbon dioxide content in the exhaled air, in ventilated patients, and in certain cases this is even mandatory. In this measurement procedure, known as capnometry, the measurement of the end-tidal carbon dioxide content is carried out using chemical indicators or infrared spectroscopy. By means of capnometry, additional information can be obtained both in ventilated patients and in spontaneously breathing patients who are receiving ventilatory support, for example, on the basis of which not only therapeutic decisions can be made, but which at the same time increase a patient's safety. If a patient is ventilated with an endotracheal tube, capnometry provides information about the position and functional status of the tube, enables an assessment of the patient's metabolic state and provides information about any complications. In order to perform such a measurement, two generally different methods are known, namely the so-called main flow method on the one hand and the auxiliary flow (side flow) method on the other. With the main flow method, a measuring cuvette is located in the hose system between the patient connection piece, usually an endotracheal tube, and a Y-piece, by means of which the carbon dioxide content is determined continuously during ventilation by measuring the infrared light absorption of the breathing gas. With the bypass method (partial flow method), a small volume of air is permanently extracted from the breathing gas stream and then fed to a detector by means of which the carbon dioxide content in the breathing gas is determined.

Ultimately, capnometry is an important tool for safely monitoring and controlling a patient's intubation, ventilation and anesthesia. In neonatology, the measurement of the end-tidal carbon dioxide fraction of the breathing gas is not usually performed close to the patient due to the comparatively low tidal volumes. This leads to the fact that the measured carbon dioxide fractions are partially subject to errors and can possibly lead to misinterpretations of the respective treatment situation or the patient's condition. Particularly for the field of neonatology, it would therefore generally be desirable to perform corresponding measurements as close to the patient as possible, i.e. in the vicinity of a patient connection piece or in the area of an adapter that connects the breathing gas supply to the patient connection piece, and without significantly increasing the dead space volume. However, the use of adapters known from the prior art to establish a connection between a breathing gas supply and a patient connector sometimes leads to a not inconsiderable increase in the dead space volume, which must be minimized, especially when ventilating or providing respiratory support to neonates. Furthermore, adapters are known which enable the withdrawal of breathing gas in areas comparatively remote from the patient, for example via a tube connection with Luer lock in the area of a heat and moisture exchanger. Such adapters tend to cause turbulence within the breathing gas stream, which in turn can lead to artifacts in the measurement of end-tidal carbon dioxide content in the breathing gas stream. Aspirating a partial breathing gas flow in an area between the patient and a filter element to determine the end-tidal carbon dioxide content by means of the bypass method (side stream method) is not advisable for safety reasons, as there is a risk of an unacceptable amount of air being aspirated from the patient's lungs if the main flow channel becomes blocked, for example if a filter becomes clogged.

In this context, an adapter for establishing a gas-tight connection between a breathing gas supply and an endotracheal tube, which can be used for ventilating premature and newborn infants, is known from DE 41 30 724 A1. The adapter described has an integrated heat and moisture exchanger (HME filter) to minimize carbonic acid retention and an additional connection port for patient-side connection to a pressure monitoring system. A problem with the adapter described is that in the event of an unintentional disconnection of the hose leading to the pressure monitoring system, uncontrolled breathing gas can escape from the adapter.

SUMMARY

Based on the solutions known from the prior art as well as the problems described above, the invention is based on an object of specifying an adapter for establishing a gas-tight connection between a breathing gas (respiratory gas) supply and a patient connection piece, which is characterized by a compact configuration combined with a low dead space and, in addition, enables a simple and safe possibility of realizing a measurement of the end-tidal carbon dioxide content of the breathing gas. Furthermore, it should be possible to combine the adapter to be specified with a filter element, a heat exchanger and/or a moisture exchanger without the risk of adversely affecting the ventilation or respiratory support of a patient. It is generally of particular importance that, despite the realization or performance of an end-tidal carbon dioxide measurement, the ventilation pressure within the adapter does not drop inadmissibly and, in the case of an aspirating measurement, an unacceptable amount of air is extracted from the ventilated patient. Furthermore, the adapter to be specified should be as technically simple as possible and also be efficient to manufacture from an economic point of view. Furthermore, it should be possible to connect the adapter quickly and without great effort to the hose systems and components currently used for ventilation or respiratory support, or to integrate the adapter into them.

The above-described object is achieved with an adapter according to the invention as well as a set (kit) for ventilation or respiratory support as disclosed, respectively. A system for ventilation or respiratory support of a patient, which solves the task underlying the invention, is further indicated in claim 15. Advantageous embodiments of the invention are the subject of this disclosure and are explained in more detail in the following description with partial reference to the figures.

According to the invention, an adapter for providing a flow channel between a breathing gas supply and a patient connection piece, which has a first connection structure for connection to the breathing gas supply and a second connection structure for connection to the patient connection piece, has been further configured in such a way in that a bypass channel branching off from the flow channel is provided with a withdrawal opening which can be closed at least temporarily by a safety valve, and in that the safety valve is configured in such a way that the withdrawal opening is closed when a respiratory pressure prevailing in the flow channel is lower than a pressure prevailing on a side of the safety valve facing away from the flow channel. According to the invention, an adapter is thus provided which has an extraction opening which can be closed with the aid of a safety valve. The safety valve is a valve that closes the tapping opening whenever there is a negative pressure in the flow channel of the adapter relative to a pressure prevailing on the side of the safety valve facing away from the flow channel, in particular relative to an atmospheric ambient pressure prevailing in the vicinity of the adapter and thus outside the flow channel.

With the aid of the adapter configured according to the invention, it is thus possible to extract at least part of the breathing gas flow in the immediate vicinity of the patient connector, for example in the region of the distal end of an endotracheal tube, and to carry out measurements of the end-tidal carbon dioxide content of the breathing gas without the risk of an unacceptable amount of breathing gas being extracted from the main flow channel in the adapter. Of course, with the solution according to the invention, it is alternatively or complementarily possible to detect the concentration of other gases in the breathing gas, for example volatile anesthetics, by means of an aspirating measurement. An essential feature of the solution according to the invention is that, despite the additional sampling point provided on the adapter with a bypass channel, a sampling opening and a safety valve, on the one hand the dead space inside the adapter is kept comparatively small and, on the other hand, an uncontrolled outflow of the breathing gas from the flow channel, for example if there is an increase in flow resistance inside the flow channel, is prevented. This ensures that, even if a suction measurement of the end-tidal carbon dioxide content is carried out, the flow channel and thus the patient are not deprived of an acceptable amount of breathing gas.

Preferably, the sampling opening is located on the side of the adapter facing the patient, so that the sampling opening is positioned as close as possible to the second connection structure arranged at the proximal end and thus as close as possible to the patient connection piece. With the aid of the adapter configured according to the invention, it is thus possible to measure the end-tidal carbon dioxide content of the breathing gas close to the patient. The safety valve provided closes the sampling opening and thus the sampling point intended for gas sampling as soon as the ventilation pressure in the flow channel is lower than the pressure prevailing on the side of the safety valve facing away from the flow channel, i.e. in particular lower than the atmospheric ambient pressure. This ensures, for example, that as soon as the ventilation pressure prevailing in the flow channel falls below the ambient pressure during a suction measurement, for example due to an at least partial blockage of the flow channel, the safety valve closes the sampling opening and no further breathing gas is sucked out of the flow channel or the patient's lungs. A ventilator used for ventilation or respiratory support will then detect the change in flow characteristics in the flow channel and provide an appropriate alarm in the event of a threshold (limit) value violation.

According to a special further development of the invention, a filter element, a heat exchanger and/or a moisture exchanger is arranged in the flow channel of the adapter. By integrating such a component into the adapter, an adapter with increased functionality is provided which is nevertheless characterized by a comparatively small installation space.

Particularly preferably, the adapter has a combined heat and moisture exchanger, a so-called HME filter (Heat and Moisture Exchanger).

The filter element, the heat exchanger and/or the moisture exchanger, in particular a combined heat and moisture exchanger, is advantageously arranged on the side of the tapping opening facing the first connection structure of the adapter for connection to the breathing gas supply. The respective component used is then arranged distal to the extraction opening that can be closed with the safety valve, so that the bypass channel therefore branches off from the flow channel on the side of a corresponding element facing the second connection structure. Due to this technical solution, it is ensured that even if there is a blockage of the filter element, the heat exchanger and/or the moisture exchanger, an excessive amount of breathing gas is not extracted via the extraction opening and the bypass channel, even when performing an extraction measurement. In this case, the safety valve closes the sampling opening as soon as the respiratory pressure inside the flow channel on the side facing the patient of the respective filter element, heat exchanger and/or moisture exchanger used falls below the ambient atmospheric pressure prevailing in the vicinity of the adapter, so that again the flow channel and the patient are not deprived of an unacceptable amount of breathing gas.

By providing an adapter configured according to the invention which additionally has a filter element, a heat exchanger and/or a moisture exchanger, in particular a combined heat and moisture exchanger, it is achieved that such an element does not have to be additionally integrated into the ventilation system. A further increase in dead space caused by this is thus avoided in an advantageous manner.

In a special further development of the invention, the bypass channel has, on a side of the safety valve facing away from the flow channel, a connection structure for connecting a hose for an at least intermittent extraction of breathing gas, preferably effected by suction. This connection structure of the extraction point preferably has a tubular contour, which can have a constant outer diameter or be of conical configuration, so that an extraction hose can be plugged onto the connection structure. According to a further development, a connection between the tapping point and a tapping tube for producing a gas-tight connection between the bypass channel and a suction unit may be established via a connecting element in the form of a Luer lock. Such a connecting element reliably prevents unintentional disconnection of the sampling tube from the adapter. Should an unintentional disconnection of the sampling point and the sampling tube nevertheless occur, the safety valve provided according to the invention in the area of the sampling opening ensures that even in this case breathing gas can only escape from the flow channel into the environment until the pressure in the bypass channel on the side opposite the flow channel, in this case the ambient pressure, is greater than the ventilation pressure in the flow channel of the adapter. As soon as the ventilation pressure in the flow channel of the adapter is lower than the ambient pressure, the safety valve immediately closes the extraction opening.

In a special embodiment of the invention, the safety valve has a movably mounted valve element on which both the ventilation pressure prevailing in the flow channel and the pressure prevailing on the side of the safety valve facing away from the flow channel act. Depending on the prevailing pressures or the pressure conditions, the valve element is moved, i.e. displaced, shifted, folded and/or rotated, in such a way that the sampling opening is either opened or closed. In this case, the valve element is arranged and configured in such a way that the sampling opening and thus the bypass channel is closed as soon as the ventilation pressure in the flow channel of the adapter falls below a pressure that acts on the valve element on the side facing away from the flow channel. In this context, a suitable sealing surface may be arranged on the side of the valve element facing the extraction opening and/or the side facing the bypass channel.

According to a very special further development of the invention, it is provided that the safety valve has a valve opening to an environment of the adapter in which an atmospheric ambient pressure prevails, and the valve opening is arranged in such a way that the atmospheric ambient pressure prevailing in the environment of the adapter acts on the valve element via the valve opening, so that the valve element closes the extraction opening as soon as the ambient pressure is greater than the ventilation pressure prevailing in the flow channel. If the ventilation pressure rises above the ambient pressure again, the valve element of the safety valve opens and at least part of the breathing gas flowing in the flow channel can be withdrawn again via the bypass channel and the withdrawal opening of the adapter.

Alternatively or in addition, the safety valve may have a spring element which acts on the valve element in such a way that the valve element closes the extraction opening as soon as the ventilation pressure in the flow channel of the adapter falls below a pressure which prevails on the side of the safety valve facing away from the flow channel, in particular the ambient pressure.

In a further particular embodiment of the invention, it is provided that the tapping (extraction) point of the adapter has an additional closure element, for example in the form of a push-on cap, a screw closure or a rotary snap closure, so that the extraction (tapping) is gas-tight sealed as soon as no extraction tube or other component is connected to the tapping point of the adapter.

Furthermore, a special development provides that the adapter has a first connection structure for attaching a Y-piece and/or a breathing tube of a breathing gas supply. It is essential in this case that the adapter can be connected quickly and securely to a corresponding component of a breathing gas supply. In an advantageous manner, the first connection structure is configured in such a way that, although a rapid connection of the adapter to the correspondingly provided component can take place, an unintentional disconnection of the connection is at least made more difficult. In this context, the first connection structure may be tubular or slightly conical in shape to enable easy connection to a Y-piece and/or a breathing tube of a breathing gas supply.

A further special embodiment of the invention provides that the second connection structure is configured to establish a secure and gas-tight connection with a tube, in particular with an endotracheal tube and particularly preferably with an endotracheal tube suitable for the ventilation of infants, premature infants and/or neonates. For this purpose, the second connection structure is also preferably tubular and/or has at least partially a conical section so that the outer diameter is reduced in the direction of the patient side.

The second connection structure of the adapter may be con figured in such a way that a tube, in particular a nasal tube, a nose mask and/or a mouth-nose mask can be attached to the second connection structure.

In addition to an adapter, the invention relates to a set for ventilation or respiratory support with an adapter according to the invention, which is configured according to at least one of the technical embodiments described above, and with a patient connector in the form of a nasal tube, a nasal mask, an additional adapter element and/or an oral nasal mask attached to the second connection structure of the adapter. The invention also relates to a set for ventilation or respiratory support with an adapter according to the invention, which is configured according to at least one of the technical embodiments described above, and with a tube attached to the second connection structure of the adapter, in particular with an endotracheal tube. A set for ventilation or respiratory support of a patient according to the invention is advantageously configured such that it can be used for ventilation or respiratory support of an infant, a premature infant and/or a neonate. In general an adapter configured according to the invention may be combined with a patient connection piece selected according to need.

In addition, the invention also relates to a system for ventilation or respiratory support of a patient with a ventilator or anesthesia device and with an adapter connected thereto and embodied according to the invention and according to one of the embodiments described above such that at least temporarily a gas-tight connection exists between an outlet of the ventilator or anesthesia device and the flow channel of the adapter. The ventilation or respiratory support system according to the invention is thus based on the advantageous combination of an adapter embodied according to the invention for connecting a breathing gas supply to a patient connector and a ventilation or anesthesia device. A corresponding system enables the ventilation or respiratory support of a patient in a particularly advantageous manner, in which case a particularly safe measurement and monitoring of the end-tidal carbon dioxide content of the breathing gas flow can be realized.

In the following, without limiting the general idea of the invention, the invention is explained in more detail by means of specific embodiments with reference to the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
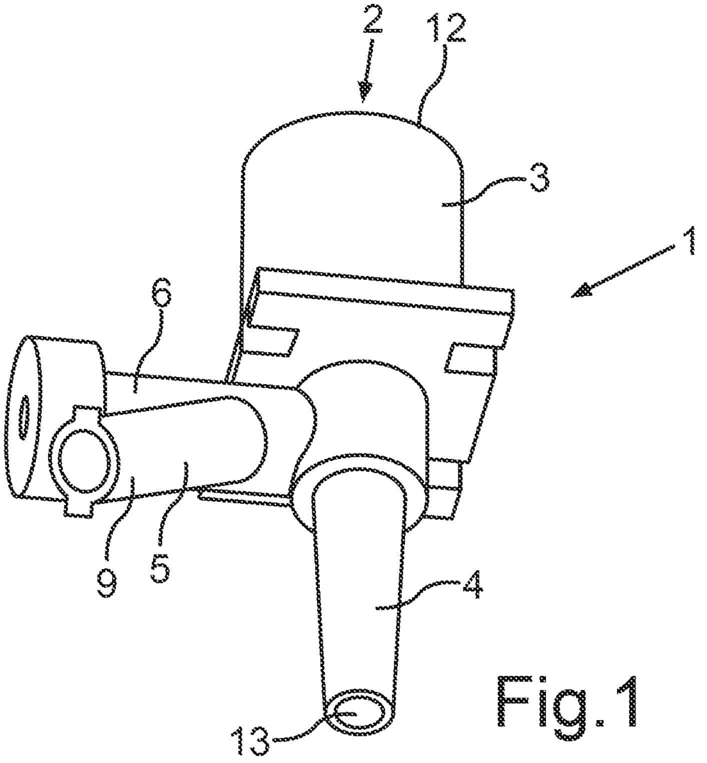
FIG. 1 is a perspective view of an adapter configured according to the invention for connecting a breathing gas supply to a patient connector.

Referring to the drawings, FIG. 1 shows a perspective view of an adapter 1 configured according to the invention for connecting a breathing gas (respiratory gas) supply to a patient connection piece. The adapter 1 has a first connection structure 3 to which a breathing tube or a Y-piece of a breathing gas supply can be attached. A second connection structure 4 is provided at the opposite proximal end, i.e. near the patient during operation, to which a tube, in particular an endotracheal tube for ventilating a neonate, can be attached. An essential feature of the adapter 1 shown is that a bypass channel 5 with an extraction (sampling/withdrawal) opening 7 branches off from a flow channel 2, which connects the adapter ends to the first and second connection structures 3, 4 in a gas-tight manner, via which a part of the breathing gas flow flowing in the flow channel 2 can be withdrawn at least temporarily and supplied via a withdrawal connection 9, for example to a tube not shown in this view. According to the embodiment shown in FIG. 1, the extraction connection 9 is tubular, so that an extraction hose can be plugged on for extracting at least part of the breathing gas flowing in the flow channel 2. Furthermore, the extraction connection (sampling port) 9 has a connection structure such that a sampling tube can be firmly attached to the extraction connection 9 in a detachable manner by means of a Luer lock closure. A portion of the breathing gas flowing in the flow channel 2 can be extracted via such an extraction connection 9 and sampling tube and preferably fed for a measurement of the end-tidal carbon dioxide content of the breathing gas.

Furthermore, the adapter 1 shown in FIG. 1 has a safety valve 6 which closes the extraction opening 7 of the bypass channel 5 as a function of a ventilation pressure prevailing in the flow channel 2. The safety valve 6 closes the extraction opening 7 as soon as the ventilation pressure within the flow channel 2 of the adapter 1 drops below the pressure prevailing on the side of the safety valve 6 facing away from the flow channel 2. In the embodiment example shown in FIG. 1, the safety valve 6 closes the extraction opening 7 as soon as the ventilation pressure in the flow channel 2 of the adapter 1 falls below an ambient atmospheric pressure prevailing in the vicinity of the adapter 1. An appropriately configured safety valve 6 ensures that in the event of an impermissible drop in pressure within the flow channel 2 of the adapter 1, for example due to an at least partial blockage of the flow channel 2 during a suction measurement, an impermissible extraction of breathing gas from the flow channel 2, and possibly from the patient's lungs, is prevented.

Figure 2A:
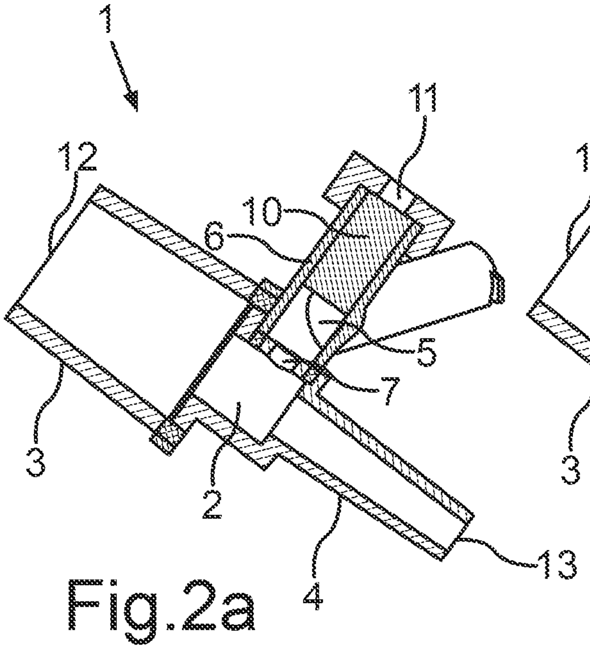
FIG. 2*a* is a sectional view of an adapter configured according to the invention for connecting a breathing gas supply to a patient connector, shown in an operating position with the sampling opening open.
Figure 2B:
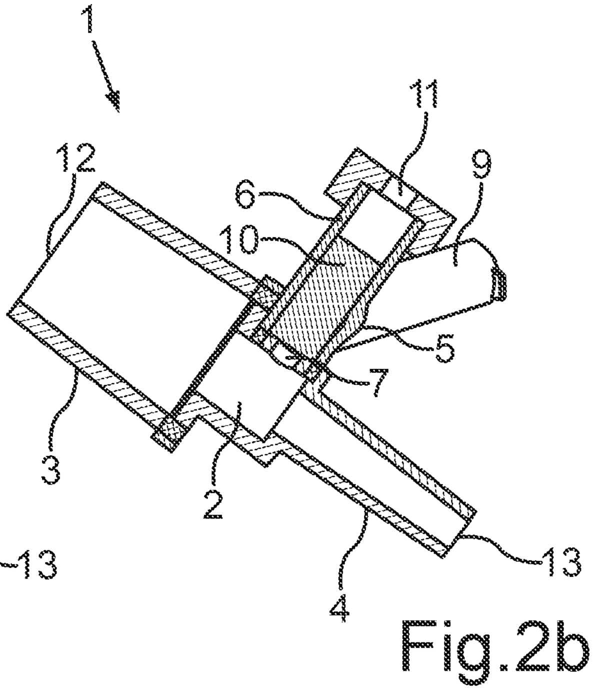
FIG. 2*b* is a sectional view of an adapter configured according to the invention for connecting a breathing gas supply to a patient connector, shown in an operating position with the sampling opening closed.

FIGS. 2*a* and 2*b* shows a sectional view of an adapter 1 configured according to the invention for connecting a breathing gas supply to a patient connector both in an operating position with an open extraction (tapping) opening 7 and in an operating position with a closed extraction opening 7. FIG. 2*a* shows the adapter 1 in an operating state with an open extraction opening 7, whereas FIG. 2*b* shows the adapter 1 in an operating state with a extraction opening 7 closed by a safety valve 6.

A flow channel 2 for conveying the breathing gas extends between a first end 12 with a first connection structure 3, which in operation is connected to an element of a breathing gas supply, for example a ventilation tube, and a second end 13 with a second connection structure 4, which in operation is connected to a patient connection piece, for example an endotracheal tube. The bypass channel 5 with the extraction opening 7 for at least temporarily extracting part of the breathing gas flowing in the flow channel 2 branches off from this flow channel 2. In addition, the adapter 1 has an extraction (sampling) connection 9 for attaching an extraction hose, with which a connection can be made to a device for measuring the carbon dioxide content of a partial breathing gas stream extracted from the flow channel 2. According to the embodiment shown in FIG. 1, the extraction connection 9 is tubular, so that an extraction hose can be plugged on for extracting at least part of the breathing gas flowing in the flow channel 2. Furthermore, the extraction connection 9 has a connection structure such that a sampling tube can be firmly attached to it in a detachable manner by means of a Luer lock.

Furthermore, a safety valve 6 with a movably arranged valve element 10 is provided, with which the extraction opening 7 can be closed as a function of a ventilation pressure prevailing in the flow channel 2.

According to the operating situation shown in FIG. 2*a*, the safety valve 6 and the valve element 10 are in the open position, in which breathing gas can be withdrawn from the flow channel 2 of the adapter 1 via the extraction opening 7 and the bypass channel 5, in particular extracted from it, during an operation in order to carry out a measurement of the end-tidal carbon dioxide content. As soon as an operating state occurs in which the ventilation pressure in the flow channel 2 drops below a pressure, in this case an atmospheric ambient pressure in the vicinity of the adapter 1, which prevails on the side of the safety valve 6 facing away from the flow channel 2, the extraction opening 7 is closed by the valve element 10 of the safety valve 6. This operating state, in which the extraction opening 7 is closed by the valve element 10 of the safety valve 6, is shown in FIG. 2*b*.

The safety valve 6 is configured in such a way that the valve element 10 can be moved between two positions, namely a position in which the extraction opening 7 is open and a position in which the extraction opening 7 is closed. According to the embodiment shown in FIG. 2, the safety valve 6 has a valve opening 11 through which the ambient pressure prevailing in the vicinity of the adapter 1 acts on the valve element 10. In contrast, the ventilation pressure prevailing in the flow channel 2 of the adapter 1 acts on the opposite side of the valve element 10, so that the valve element 10 is displaced or held in the corresponding position depending on the two pressures or pressure forces acting on the valve element 10 in opposite directions.

In the operating state shown in FIG. 2*b*, the ambient pressure acting on the valve element 10 of the safety valve 6 via the valve opening 7 is greater than the ventilation pressure prevailing in the flow channel 2 of the adapter 1, which acts on the valve element 10 via the extraction opening 7 of the bypass channel 5. The extraction opening 7 is therefore closed by the valve element 10. Compared to the operating state shown in FIG. 2*a*, in which the valve element 10 of the safety valve 6 is in an open position, the pressure conditions are reversed in the operating situation shown in FIG. 2*b*.

Figure 3B:
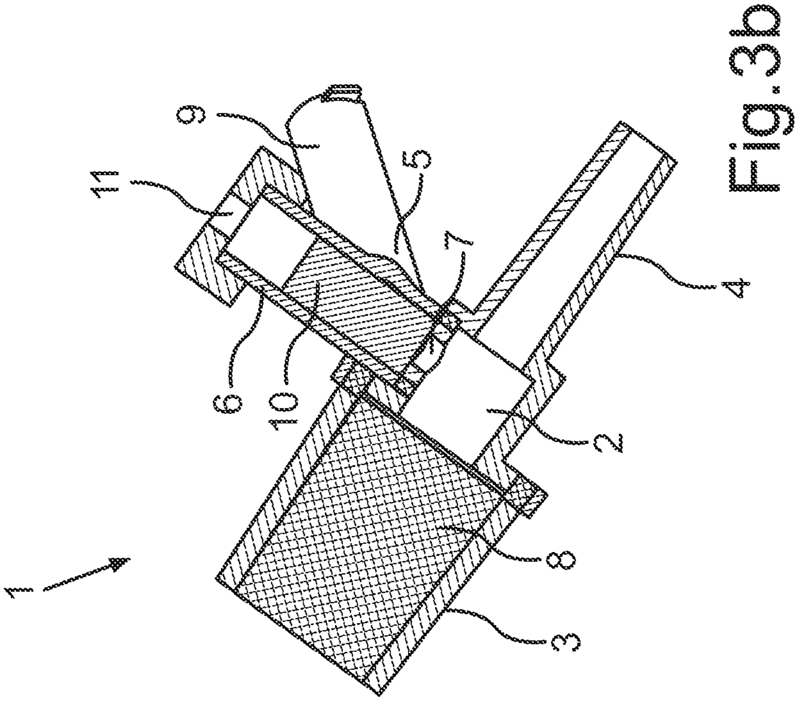
FIG. 3*b* is a sectional view of an adapter configured according to the invention with integrated heat and moisture exchanger for connecting a breathing gas supply to a patient connector, shown in an operating position with the sampling opening closed.
Figure 3A:
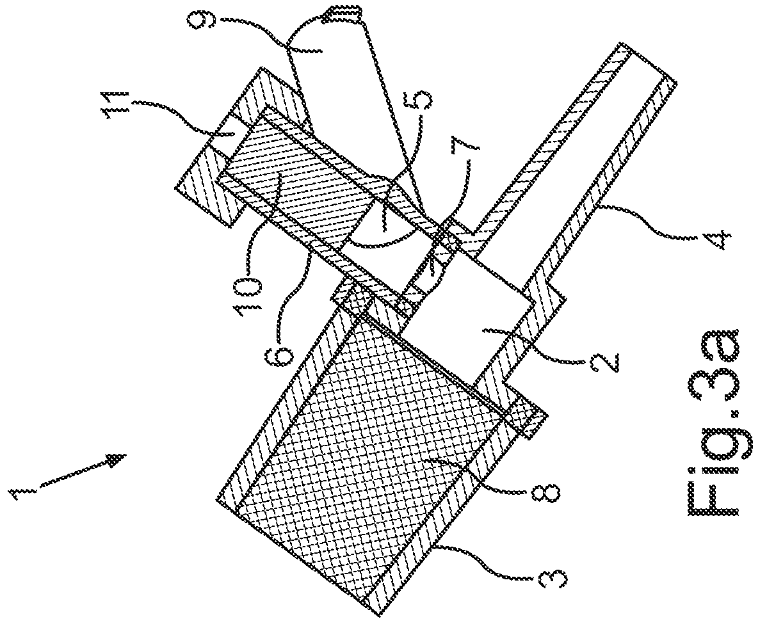
FIG. 3*a* is a sectional view of an adapter configured according to the invention with integrated heat and moisture exchanger for connecting a breathing gas supply to a patient connector, shown in an operating position with the sampling opening open.

In addition, FIGS. 3*a* and 3*b* shows a sectional view of an adapter 1 configured according to the invention with an element for treating the breathing gas 8, in this case an integrated heat and moisture exchanger, for connecting a breathing gas supply to a patient connection piece in an operating position with the extraction opening 7 open and in an operating position with the extraction opening 7 closed. FIG. 3*a* again shows the adapter 1 in an operating state with the withdrawal opening 7 open, while FIG. 3*b* shows the adapter 1 in an operating state with the withdrawal opening 7 closed by a safety valve 6. The configuration and functionality with regard to the flow guidance of the breathing gas, the withdrawal possibility of a partial breathing gas flow as well as the safety valve 6 provided correspond to those of the adapter 1 shown in FIGS. 2*a* and 2*b*. Also in the adapter 1 shown in FIGS. 3*a* and 3*b*, the withdrawal opening 7 is closed by the valve element 10 of the safety valve 6 as soon as the ambient atmospheric pressure prevailing in an environment of the adapter 1 is greater than the respiratory pressure in the flow channel 2 of the adapter 1. In contrast to the adapter shown in FIG. 2, the adapter shown in FIG. 3 additionally has an element for treating the breathing gas 8 in the form of a combined heat and moisture exchanger, a so-called HME filter, which is arranged on a side of the extraction opening 7 of the branching bypass channel 5 facing the first connection structure 3. With the aid of such a combined heat and moisture exchanger, both temperature control and humidification or dehumidification of the breathing gas flow can be ensured as required.

Due to the safety valve 6 configured according to the invention, it is also ensured in an advantageous manner in the case of an adapter 1 according to FIGS. 3*a* and 3*b* that even if an at least partial blockage of the combined heat and moisture exchange should occur during the performance of an aspirating measurement of the end-tidal carbon dioxide content, an unacceptable amount of breathing gas is not sucked in via the extraction opening 7 of the bypass channel 5. This is in turn achieved by the fact that the extraction opening 7 is closed by the valve element 10 of the safety valve 6 as soon as the breathing pressure prevailing in the flow channel 2 falls below the ambient atmospheric pressure prevailing in the vicinity of the adapter 1.

Figure 4:
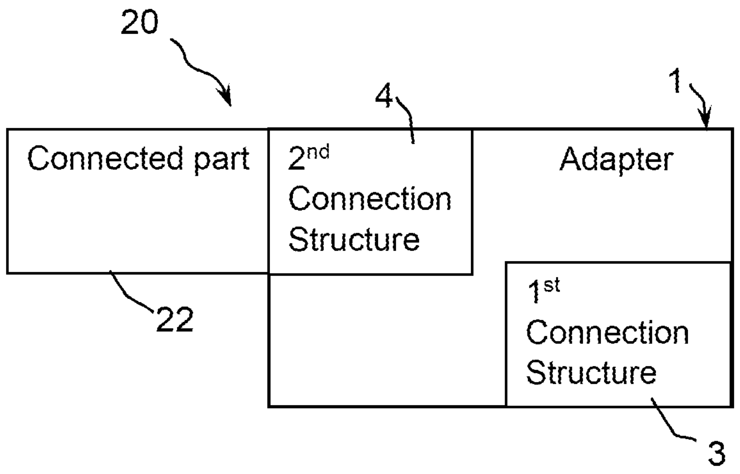
FIG. 4 is a schematic view showing a ventilation or respiratory support set comprising an adapter and a connected part such as a patient fitting.

FIG. 4 schematically shows a ventilation or respiratory support set 20 that comprises one of the adapters 1 of FIG. 2*a*, 2*b* or 3*a*, 3*b* for establishing a flow channel between a breathing gas supply and a patient fitting in combination with a connected/connectable part (patient fitting and/or tube with patient fitting) 22 configured to attach to the second connection structure 4 and which is schematically shown attached to the second connection structure 4. The connected/connectable part 22 comprises one or more of a nasal mask or an oral-nasal mask and a tube. The mask and/or tube 22 may advantageously be configured for ventilation of one or more of infants, premature infants and neonates.

Figure 5:
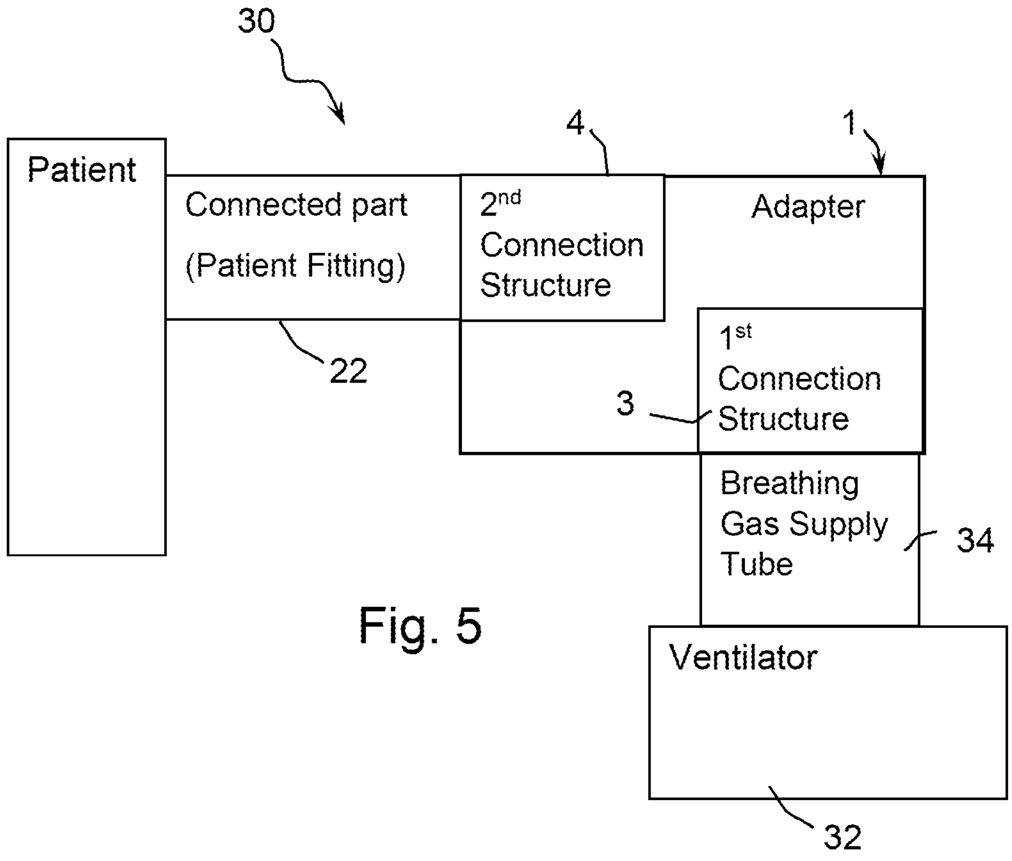
FIG. 5 is a schematic view showing a system for ventilating or providing respiratory support to a patient, comprising a ventilator or anesthesia device and an adapter.

FIG. 5 schematically shows a system 30 for ventilating or providing respiratory support to a patient. The system 30 comprises one of the adapters 1 of FIG. 2*a*, 2*b* or 3*a*, 3*b* and a ventilator or anesthesia device 32 connected to the adapter 1, particularly connected via a breathing gas supply 34 tube and the first connection structure 3 and forming a gas-tight connection between an outlet of the ventilator or anesthesia device 32 and the flow channel 2 of the adapter 1. The connected/connectable part (patient fitting and/or tube with patient fitting) 20 is attached to the second connection structure 4.

With the aid of the technical solution provided in accordance with the invention, i.e. an adapter 1 with an additional, automatic safety valve 6, it is possible, on the one hand, to measure the end-tidal carbon monoxide content in the breathing gas close to the patient and, on the other hand, to ensure that an impermissible drop in pressure in the flow channel 2 of the adapter 1 and thus excessive suction of breathing gas from the flow channel 2 and thus from the patient's lungs is reliably prevented. The adapter 1 according to the invention has a comparatively simple configuration in this respect and enables not only reliable operation as well as safe operation, but also its effective and inexpensive manufacture.

While specific embodiments of the invention have been shown and described in detail to illustrate the application of the principles of the invention, it will be understood that the invention may be embodied otherwise without departing from such principles.

LIST OF REFERENCE SYMBOLS

1 Adapter
2 Flow channel
3 First connection structure
4 Second connection structure
5 Bypass channel
6 Safety valve
7 Extraction opening
8 Breathing gas treatment element
9 Extraction connection (sampling part)
10 Valve element
11 Valve opening
12 First end
13 Second end
20 Ventilation or respiratory support set (kit)
22 Connected part (patient fitting and/or tube with patient fitting)
30 System for ventilating or providing respiratory support to a patient
32 Ventilator or anesthesia device
34 Breathing gas supply

What is claimed is:

1. An adapter for establishing a flow channel between a breathing gas supply and a patient fitting, the adapter comprising:

a first connection structure configured to connect to the breathing gas supply;

a second connection structure configured to connect to the patient fitting;

a bypass channel branching off from the flow channel, the bypass channel having an extraction opening; and a safety valve configured to close the extraction opening upon a ventilation pressure prevailing in the flow channel being lower than a pressure prevailing on a side of the safety valve facing away from the flow channel;

wherein the safety valve comprises a valve element and a valve opening to an environment of the adapter; and the valve opening is arranged such that an atmospheric ambient pressure prevailing in an environment of the adapter acts on the valve element via the valve opening so that the valve element closes the extraction opening when ambient pressure is greater than ventilation pressure prevailing in the flow channel.

2. An adapter according to claim 1, further comprising a breathing gas treatment element for breathing gas treatment, the breathing gas treatment element being arranged in the flow channel and comprising one or more of a filter element, a heat exchanger and a moisture exchanger.

3. An adapter according to claim 2, wherein the bypass channel branches off on a side of the breathing gas treatment element facing the second connection structure.

4. An adapter according to claim 1, wherein the bypass channel comprises an extraction connection on a side of the safety valve facing away from the flow channel, the extraction connection being configured to connect a hose for at least intermittent gas extraction form the flow channel.

5. An adapter according to claim 1, wherein the first connection structure is configured to attach to one or more of a Y-piece and a ventilation tube.

6. An adapter according to claim 1, wherein the second connection structure is at least partially conical.

7. An adapter according to claim 1, wherein the second connection structure is configured to attach to one or more of a nose mask and an oral mask.

8. An adapter according to claim 1, wherein the second connection structure is configured for at least indirect attachment of a tube.

9. An adapter according to claim 1, wherein the safety valve is configured such that the extraction opening is closed when a ventilation pressure prevailing in the flow channel is lower than an atmospheric ambient pressure prevailing in an environment of the adapter.

10. An adapter according to claim 1, wherein the safety valve comprises a movably mounted valve element on which ventilation pressure prevailing in the flow channel acts and on which pressure prevailing on the side of the safety valve facing away from the flow channel acts.

11. A ventilation or respiratory support set comprising:

an adapter for establishing a flow channel between a breathing gas supply and a patient fitting, the adapter comprising:

a first connection structure configured to connect to the breathing gas supply;

a second connection structure configured to connect to the patient fitting;

a bypass channel branching off from the flow channel, the bypass channel having an extraction opening; and a safety valve configured to close the extraction opening upon a ventilation pressure prevailing in the flow channel being lower than a pressure prevailing on a side of the safety valve facing away from the flow channel;

wherein the safety valve comprises a valve element and a valve opening to an environment of the adapter; and the valve opening is arranged such that an atmospheric ambient pressure prevailing in an environment of the adapter acts on the valve element via the valve opening so that the valve element closes the extraction opening when ambient pressure is greater than ventilation pressure prevailing in the flow channel; and a nasal or an oral-nasal mask or a tube configured to attach to the second connection structure.

12. A ventilation or respiratory support set according to claim 11, wherein the tube is configured for ventilation of one or more of infants, premature infants and neonates.

13. A system for ventilating or providing respiratory support to a patient, comprising:

an adapter for establishing a flow channel between a breathing gas supply and a patient fitting, the adapter comprising:

a first connection structure configured to connect to the breathing gas supply;

a second connection structure configured to connect to the patient fitting;

a bypass channel branching off from the flow channel, the bypass channel having an extraction opening; and a safety valve configured to close the extraction opening upon a ventilation pressure prevailing in the flow channel being lower than a pressure prevailing on a side of the safety valve facing away from the flow channel;

wherein the safety valve comprises a valve element and a valve opening to an environment of the adapter; and the valve opening is arranged such that an atmospheric ambient pressure prevailing in an environment of the adapter acts on the valve element via the valve opening so that the valve element closes the extraction opening when ambient pressure is greater than ventilation pressure prevailing in the flow channel; and a ventilator or anesthesia device connected to the adapter and forming a gas-tight connection between an outlet of the ventilator or anesthesia device and the flow channel of the adapter.

14. A system according to claim 13, wherein the adapter further comprises a breathing gas treatment element for breathing gas treatment, the breathing gas treatment element being arranged in the flow channel and comprising one or more of a filter element, a heat exchanger and a moisture exchanger.

15. A system according to claim 14, wherein the bypass channel branches off on a side of the breathing gas treatment element facing the second connection structure.

16. A system according to claim 13, wherein the bypass channel comprises an extraction connection on a side of the safety valve facing away from the flow channel, the extraction connection being configured to connect a hose for at least intermittent gas extraction form the flow channel.

17. A system according to claim 13, wherein the safety valve is configured such that the extraction opening is closed when a ventilation pressure prevailing in the flow channel is lower than an atmospheric ambient pressure prevailing in an environment of the adapter.

18. A system according to claim 13, wherein the safety valve comprises a movably mounted valve element on which ventilation pressure prevailing in the flow channel acts and on which pressure prevailing on the side of the safety valve facing away from the flow channel acts.

19. A system according to claim 13, wherein the first connection structure is configured to attach to one or more of a Y-piece and a ventilation tube.

20. A system according to claim 13, wherein the second connection structure is configured to attach to one or more of a nose mask, an oral mask and at least indirectly a tube.

* * * * *